(12) United States Patent
Burton et al.

(10) Patent No.: US 7,992,560 B2
(45) Date of Patent: Aug. 9, 2011

(54) ADAPTABLE BREATHING MASK

(75) Inventors: David Burton, Camberwell (AU); Fred Blochlinger, Mt. Eliza (AU)

(73) Assignee: Compumedics Limited, Abbotsford (AU)

(*) Notice: Subject to any disclaimer, the term of this patent is extended or adjusted under 35 U.S.C. 154(b) by 878 days.

(21) Appl. No.: 11/145,300

(22) Filed: Jun. 3, 2005

(65) Prior Publication Data
US 2006/0032504 A1 Feb. 16, 2006

Related U.S. Application Data

(60) Provisional application No. 60/576,520, filed on Jun. 3, 2004.

(51) Int. Cl.
*A61M 16/00* (2006.01)
*A61M 16/06* (2006.01)

(52) U.S. Cl. ......... 128/207.11; 128/206.21; 128/206.24; 128/206.26; 128/206.28; 128/207.13; 128/207.18; 128/201.23

(58) Field of Classification Search ............. 128/207.11, 128/207.13, 200.24, 201.22, 202.27, 203.29, 128/204.18, 205.25, 206.21, 206.24, 206.26, 128/206.28, 207.17, 208.18
See application file for complete search history.

(56) References Cited

U.S. PATENT DOCUMENTS

| | | | |
|---|---|---|---|
| 2,749,910 A | 6/1956 | Faulconer, Jr. | |
| 3,040,741 A | 6/1962 | Carolan | |
| 3,234,940 A | 9/1962 | Morton, Jr. | |
| 3,056,402 A * | 10/1962 | Dickinson | 128/206.27 |
| 3,315,674 A * | 4/1967 | Bloom et al. | 128/201.19 |
| 3,599,635 A * | 8/1971 | Ansite | 128/206.28 |
| 4,971,051 A * | 11/1990 | Toffolon | 128/206.26 |
| 5,533,504 A * | 7/1996 | Stamos | 128/201.18 |
| 6,120,088 A * | 9/2000 | Terranova | 296/153 |
| 6,196,223 B1 | 3/2001 | Belfer et al. | |
| 6,581,602 B2 | 6/2003 | Kwok et al. | |
| 6,615,832 B1 * | 9/2003 | Chen | 128/206.26 |
| 7,024,965 B2 * | 4/2006 | Tremblay | 81/3.2 |

(Continued)

FOREIGN PATENT DOCUMENTS

AU 841104 7/1960

(Continued)

OTHER PUBLICATIONS

Webster's Dictionary, Literature Online Reference Edition—Reference Shelf: Full Text; Webster's Third New International Dictionary, Unabridged, Copyright © 1993 Merriam-Webster, Incorporated. Published under license from Merriam-Webster, Incorporated; definition for "pad".*

*Primary Examiner* — Justine R Yu
*Assistant Examiner* — Clinton Ostrup
(74) *Attorney, Agent, or Firm* — Sughrue Mion, PLLC

(57) ABSTRACT

The present invention is a breathing mask that is fully adjustable so as to enable a comfortable and leak proof seal around a patient's face. The mask includes a frame, a cushion, a hose connector, a strap, connector, a strap, and a headgear. The present invention ensures both comfort and effectiveness by enabling a full adjustment of various components such as the angle of the strap relative to the face mask and the adjustment of the size of the headgear. Furthermore, the present invention also allows for the free rotation of certain elements in order to maintain a sufficient seal without increasing the pressure applied to the patient.

7 Claims, 10 Drawing Sheets

U.S. PATENT DOCUMENTS

| | | | |
|---|---|---|---|
| 2003/0059739 A1* | 3/2003 | Mack | 433/68 |
| 2003/0075182 A1* | 4/2003 | Heidmann et al. | 128/207.11 |
| 2003/0196662 A1* | 10/2003 | Ging et al. | 128/204.15 |
| 2004/0099272 A1 | 5/2004 | Kwok et al. | |
| 2004/0255949 A1* | 12/2004 | Lang et al. | 128/206.21 |
| 2005/0005940 A1* | 1/2005 | Gunaratnam | 128/206.27 |
| 2006/0118117 A1* | 6/2006 | Berthon-Jones et al. | 128/206.27 |

FOREIGN PATENT DOCUMENTS

| | | |
|---|---|---|
| EP | 1356842 A2 | 10/2003 |
| WO | WO 01/43804 A1 | 6/2001 |
| WO | WO 2004041342 A1 * | 5/2004 |

* cited by examiner

ADAPTABLE BREATHING MASK

RELATED APPLICATIONS

This application claims benefit of U.S. Provisional Application No. 60/576,520, filed Jun. 3, 2004, and incorporated by reference herein.

FIELD OF THE INVENTION

The present invention relates generally to a breathing mask for use in the treatment of respiratory conditions and in assisted respiration. More particularly, the present invention relates to a nasal mask for use in the treatment of sleep breathing disorders.

BACKGROUND OF THE INVENTION

Breathing masks are commonly used for the delivery of gases to patients suffering from respiratory distress or from a respiratory ailment. These masks are connected to a gas source, and are used to form a relatively leak-proof seal around a patient's face. This seal enables the patient to breathe directly from the gas source or to maintain a particular airway pressure. Breathing masks are especially integral when the patient is being treated with a specific concentration of a particular gas or if the respiratory parameters of the patient are being monitored. Such applications include, the mechanical ventilation of patients and continuous positive airway pressure (CPAP) treatments for obstructive breathing disorders.

There are a variety of known breathing masks in the art. These masks typically include a frame which connects to a hose from a gas source, a cushion that connects to the frame and which creates a seal around a patient's face, and a strap for keeping the mask in place. While most known masks work for their intended purpose, many are unable to maintain a solid seal without having to apply a large amount of pressure on the patient's face. Because of the contours of the face, there is typically a tradeoff between the effectiveness of the seal and comfort during use. If a breathing mask applies too much pressure on the patient, the mask can cause discomfort or even create facial sores. For patients who require the use of a breathing mask during sleep, the discomfort of using the prior art masks may even prevent them from obtaining sleep.

In the treatment of obstructed sleep breathing, a nasal breathing mask is worn during sleep while CPAP treatments are applied. CPAP treatments provide a continuous positive pressure into the patients airway so that the airway is not allowed to collapse upon itself, enabling the patient to breathe easier during sleep. If the nasal breathing mask leaks, an insufficient amount of pressure is generated in the airway and the patient airway may collapse upon itself causing apnea, and other forms of sleep breathing disorders. Also, patient movement during sleep may cause the mask to displace forming additional leaks. The prior art masks remedy this situation by requiring a tighter fit between the patient and the mask.

However, it is also vital that the patient be able to sleep with the mask in place, so comfort is also imperative. By applying the mask too tightly, the patient is not able to sleep with the mask on or skin lesions may appear. Consequently, there is a need for a breathing mask which is able to accommodate the contours of the human face without requiring an excessive amount of pressure to ensure a seal around the patients face.

SUMMARY

The present invention is a breathing mask that maintains a relatively leak free seal around a patient's face without resorting to the application of excess pressure on the patient's face. The present invention accomplishes this by making the masks fully adjustable, and by enabling the hose to rotate around the mask so that the hose is generally prevented from knocking the mask out of position. The subject mask includes a frame, a cushion coupled to the frame, and a connector for connecting a headgear to the frame. A hose connects the mask to a gas source.

In one embodiment, the frame cooperates with the cushion to define an air proof chamber surrounding the patients face. An aperture extends through the frame in order to allow gas to pass therethrough. A lip circumferentially surrounds the aperture and forms a quick connect interface with the hose connector. The frame also includes interfacing surfaces located on opposite longitudinal ends of the frame. These interfacing surfaces form a quick connect interface with the strap connector In one embodiment, a strap connector is used to couple the strap to the frame. The strap connector includes overlaying first plate and second plates. The first plate includes a tongue portion and a cantilevered clip portion which mate with the interfacing surfaces located on the frame. A pivot arm connects the first plate to the second plate, and enables the second plate to pivot relative to the first plate. The second plate includes locking arms which connect to the strap. The rotation of the second plate with respect to the first plate enables the patient to change the angle of the strap relative to the frame. Also, the length of the strap is adjusted by changing the position of the locking arms relative to the strap.

In one embodiment, the strap is coupled to a head gear. The headgear can be comprised of two separate C-shaped strips of material which interlock with the other along its longitudinal end. The size of the headgear is adjusted by reducing or lengthening the overlapping portions of the strips. In an alternative embodiment, the headgear includes a pair of base portions which are connected together by a headstrap. The headstrap is adjustable to accommodate varying head sizes, and may comprise two separate pieces with a fastener (such as a hook in loop fastener) connecting the two. A strap arm rotatably extends from each base portion. A neck strap extends between the two strap arms. The strap arm interlocks with the base portion in order to fix the position of the neck strap relative to the patient.

In one embodiment, a hose connector 14 includes a lip portion which is sized to be insertable within the aperture on the frame. A retaining ring couples the hose connector to the frame, while still allowing the hose connector and the hose to rotate freely about the frame. This reduces the ability of the hose to push the mask out of position

DESCRIPTION OF THE DRAWINGS

For the purpose of facilitating an understanding of the invention, there is illustrated the accompanying drawings, from an inspection of which, when considered in connection with the following description, the invention, its construction and operation, and many of its advantages should be readily understood and appreciated.

FIG. 2d is an overhead view of the mask of FIG. 2a.

FIG. 2e is a side view of the mask of FIG. 2a.

DETAILED DESCRIPTION OF THE INVENTION

The present invention relates to a breathing mask for the delivery of gas from a gas source to a patient. For the purpose of explanation only, the present invention is described with respect to an embodiment which is adapted for nasal ventilation (nasal mask). One skilled in the art can readily ascertain that the present invention is easily adapted to accommodate a number of different breathing mask applications.

Figure 1:
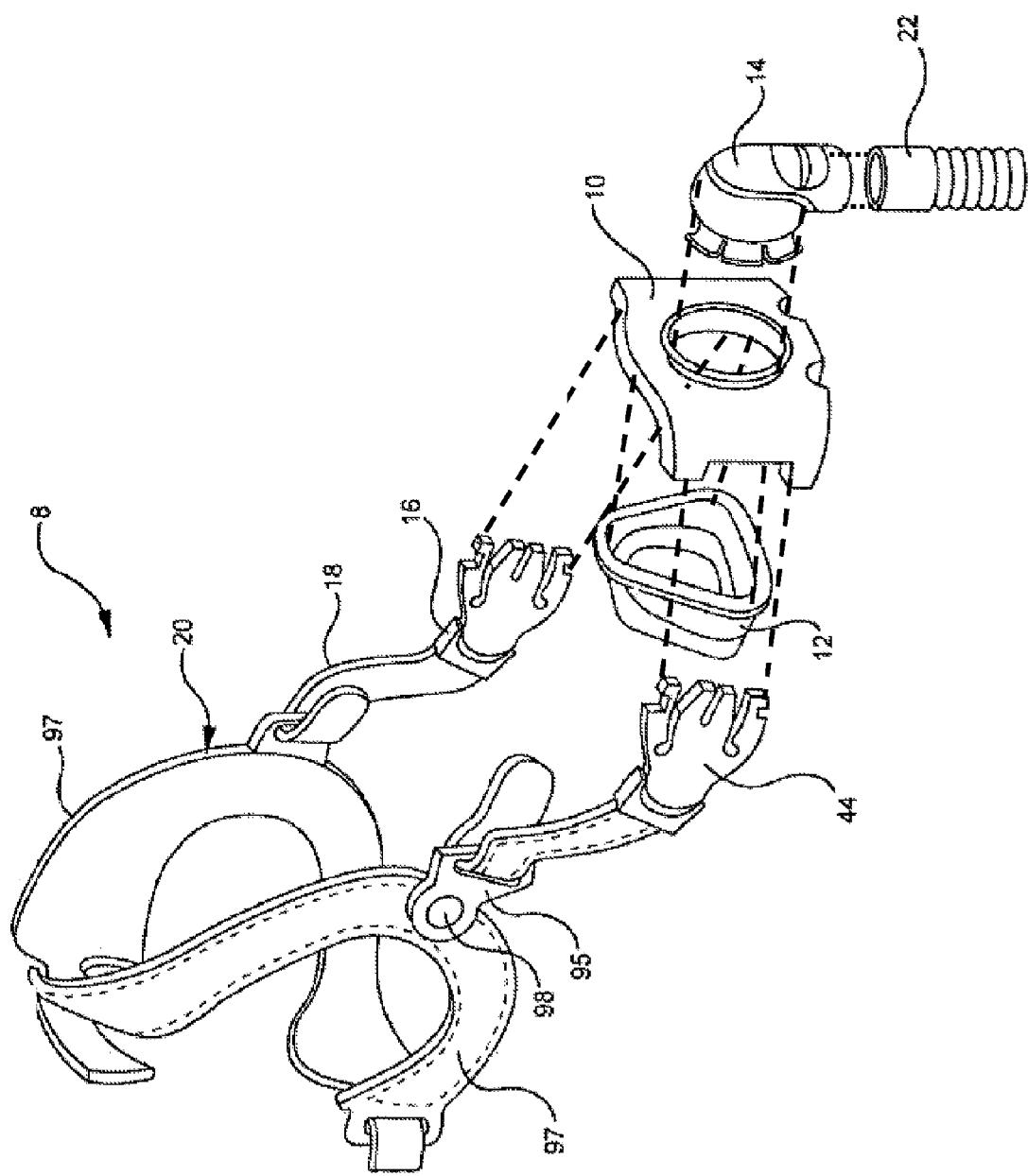
FIG. 1 an exploded view of one embodiment of the present invention.
Figure 2A:
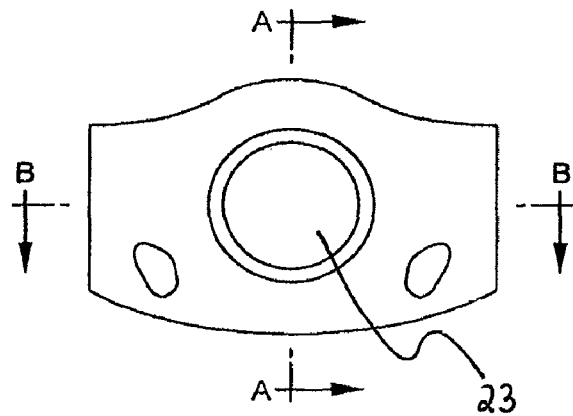
FIG. 2a is a front view of one embodiment of a frame.
Figure 2B:
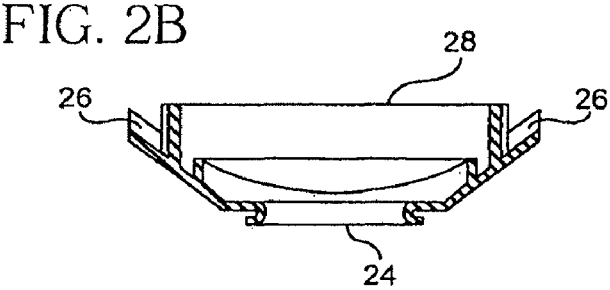
FIG. 2b is a sectional of the mask of FIG. 2a taken along lines B-B.
Figure 2C:
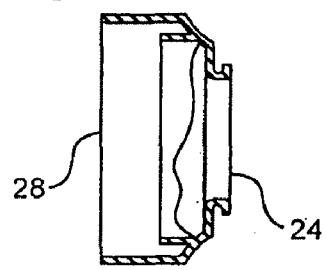
FIG. 2c is a sectional view of the mask of FIG. 2a taken along lines A-A.
Figure 2D:
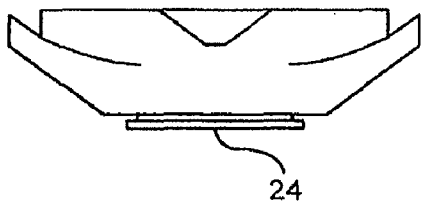
Figure 2E:
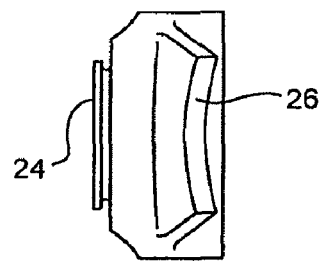

As shown in FIG. 1, in one embodiment, the present invention is a nasal breathing mask 8, sized and configured to form a seal around a patient's nose. The mask 8 includes a frame 10, a cushion 12, a hose connector 14, a strap connector 16, a strap 18, and a headgear 20. A hose 22 connects the mask 8 to a gas source (not shown). The present invention maintains a relatively leak free seal around a patient's face without resorting to the application of excess pressure on the patient's face and the frame is designed to resist displacement by the hose 22. This makes the mask 8 ideal for use in the application of CPAP to patients and for administering manual ventilation to unconscious patients.

As shown in FIGS. 1 and 2a-e, in one embodiment, the frame 10 in cooperation with the cushion defines a chamber 28 around the patient's nose. An aperture 23 enables gas to pass from the hose 22 through the frame and in to the patient's nose. A lip 24 circumferentially surrounds the aperture 23 and is sized and shaped to pneumatically interface with the hose connector 14. The frame also includes interfacing surfaces 26 located on opposite longitudinal ends of the frame 10. The interfacing surfaces 26 include structures which enable the frame to form a quick-release couple with the strap connector 16.

As shown in FIG. 1, in one embodiment, the cushion 12 connects to the frame 14 and maintains a relatively air tight seal around a nose. The cushion 12 is sized and configured to allow some mask movement without breaking its seal with the face. The cushion is made from a resilient material such as a silicone elastomer.

Figure 3A:
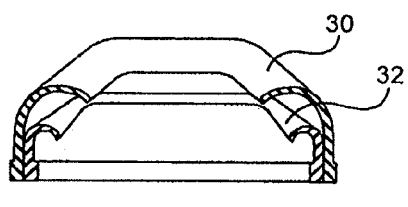
FIGS. 3a-g are sectional views of different embodies of a cushion.
Figure 3B:
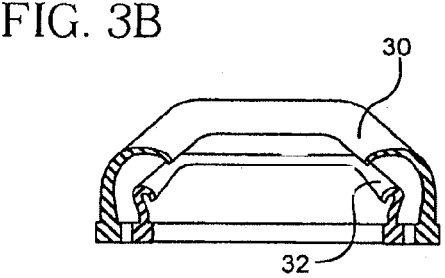
Figure 3C:
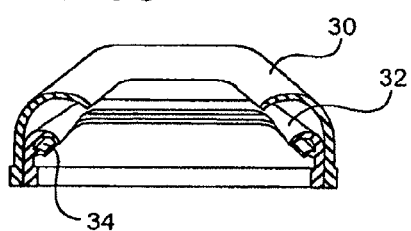
Figure 3D:
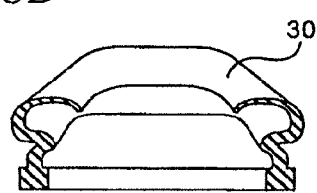
Figure 3E:
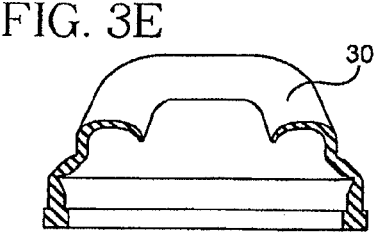
Figure 3F:
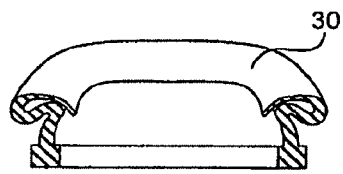
Figure 3G:
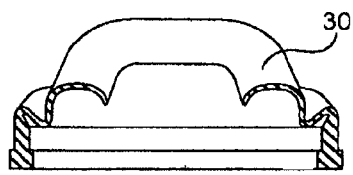

FIGS. 3a-f disclose a number of different embodiments of cushion which can be used with the present invention. FIGS. 3a-b discloses variations of a double wall design of cushion with a first membrane 30 overlaying a second membrane 32. Both the first and second membranes are curved inwardly. FIG. 3c discloses a triple wall design with a third inwardly curved membrane. FIGS. 3d-g are variations of a single wall design having a single inwardly curving membrane 30. All the cushions 12, have resilient, inwardly curving flexible membranes which are compressed during use. The cushions 12 may also include air filled pockets or any other cushion designs which are known in the art.

Figure 4A:
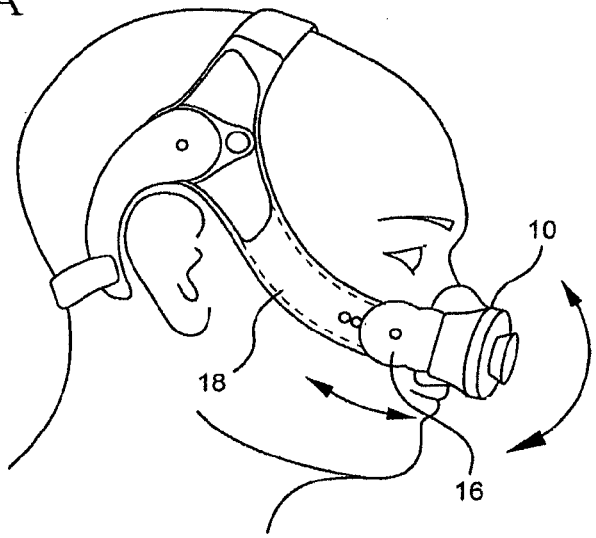
FIG. 4a is side view of one embodiment of the present invention.
Figure 4B:
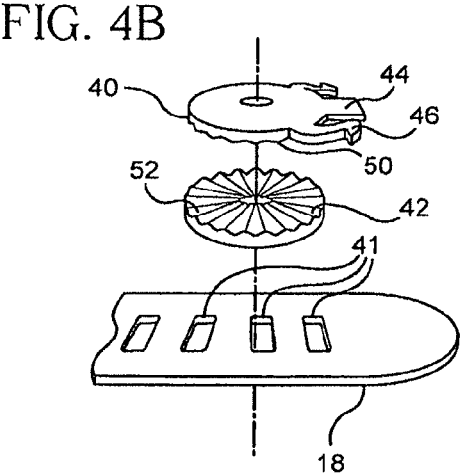
FIG. 4b is an exploded view of one embodiment of a strap connector.
Figure 4C:
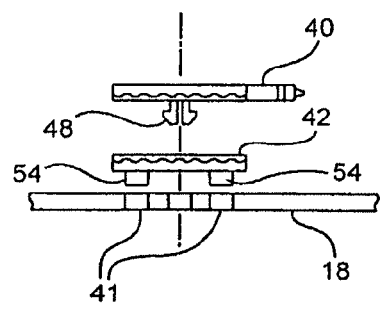
FIG. 4c is a side, exploded view of the strap connector of 4b.

As shown in FIGS. 4a-c, in one embodiment, a strap connector 16 couples the strap 18 to the frame 10. The strap connector 16 includes a first plate 40 and a second plate 42. The first plate 40 includes a tongue portion 44 and a cantilevered clip portion 46. The tongue portion 44 and the clip portion 46 mate with the interfacing surface 26 located on the frame 10. A pivot arm 48 extends from the first plate 40 and is received by the second plate 42, coupling the two, and enabling the second plate 42 to pivot relative to the first plate. Opposing interlocking surfaces 50, 52 are located on the first 40 and second plate 42 respectively. The interlocking surfaces fix the position of the second plate 42 relative to the first plate 40, thereby setting the angle of the strap 18 relative to the frame 10.

In one embodiment, the second plate 42 includes locking arms 54 which couple to the strap 18. The locking arms 54 engage apertures 41 which are positioned longitudinally along the strap 18. The rotation of the second plate 42 with respect to the first plate 40 determines the angle of the strap relative to the frame 10. Consequently, the present invention enables the strap to be adjusted lengthwise and angularly in order to establish a secure but comfortable fit with the frame 10.

As shown in FIG. 1, in one embodiment, the strap 18 is coupled to a headgear 20 via a connector 95 which is coupled to the headgear by a pivot 98. This enables the headgear 20 to rotate relative to strap 18, allowing the patient to optimize the positioning of the headgear 20. The headgear 20 is comprised of two separate C-shaped strips 97 of material which interlock with each other. The size of the headgear 20 is adjusted by reducing or lengthening the overlapping portions of the strips 97.

Figure 5A:
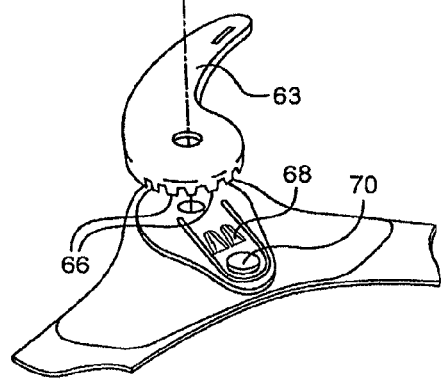
FIG. 5a is an exploded view of one embodiment of a neck strap arm.
Figure 5B:
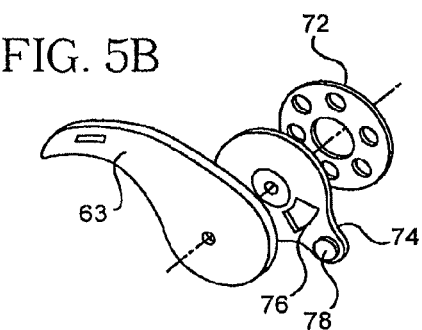
FIG. 5b is an exploded view of a second embodiment of a neck strap arm.
Figure 5C:
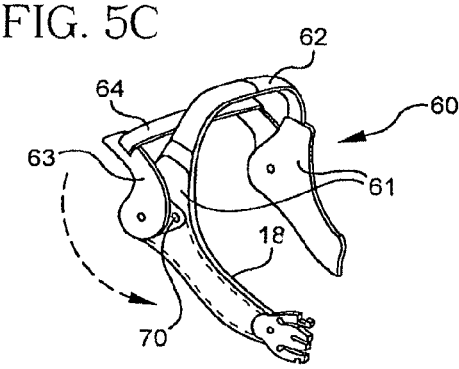
FIG. 5c-d are sequential views of the operating configuration of one embodiment of a headgear.
Figure 5D:
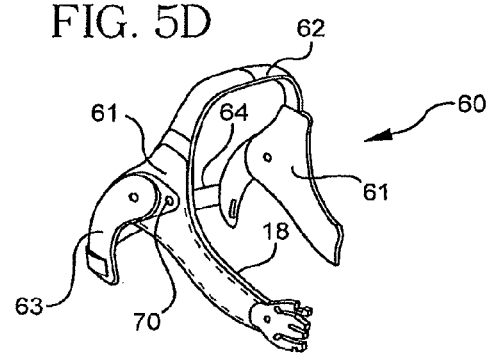

In an alternative embodiment, shown in FIGS. 5c-d, the strap 18 is integrated into the headgear 60. The headgear 60 includes a pair of base portions 61 which are connected together by a headstrap 62. The headstrap 62 is adjustable to accommodate varying head sizes, and may comprise two separate pieces with a fastener (such as a hook in loop fastener) connecting the two. The strap 18 extends from the base portion 61. A strap arm 63 extends from each base portion 61. A neck strap 64 extends between the two strap arms 63. Each strap arm 63 interlocks with the base portion 61 in order to fix the position of the neck strap 64 relative to the patients head. As shown in FIGS. 5c-d, the strap arms are first positioned to be adjacent the headstrap 62. The headgear 60 is then placed on a patient's head and the strap arms 63 rotate downward to optimally position the neck strap 64 relative to the patient's neck.

The locking mechanism for the strap arms 63 may include known ratcheting structures. One such example, as shown in 5a, involves the use of knock out spacers 66 located on the strap arms 63 and interlocking flanges 68 located on the base portion 61. In this embodiment, the flanges 68 interlock with the knock out spacers 66 to fix the angle of the strap arm 63. A release button 70, pushes the interlocking flanges 68 downward and disengages them from the knock out spacers 66.

Figure 5E:
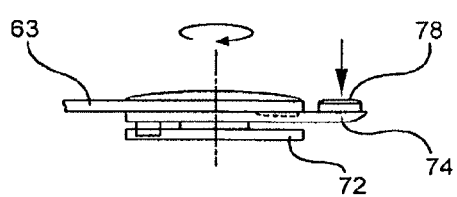
FIG. 5e is a sequential view of the embodiment of the release mechanism of FIG. 5b for a neck strap arm.
Figure 5F:
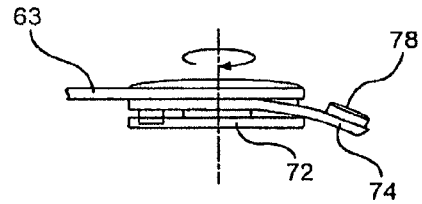

In an alternative embodiment as shown in FIGS. 5b and 5e, the rotating strap arm 63 interlocks to the base portion 61 through a triple plate mechanism. A base plate 72 is secured to the base portion 61, and the base portion 61 is coupled to the middle plate 74. A raised surface 76 on the middle plate engages the strap arm 63 and locks the -strap arm 63 in place. A release button 78 disengages the raised surface 76 from the strap arm 63, and allows the strap arm 63 to rotate freely about the base portion 61. This enables the neck strap to be positioned optimally with respect to a patient's neck.

Figure 6A:
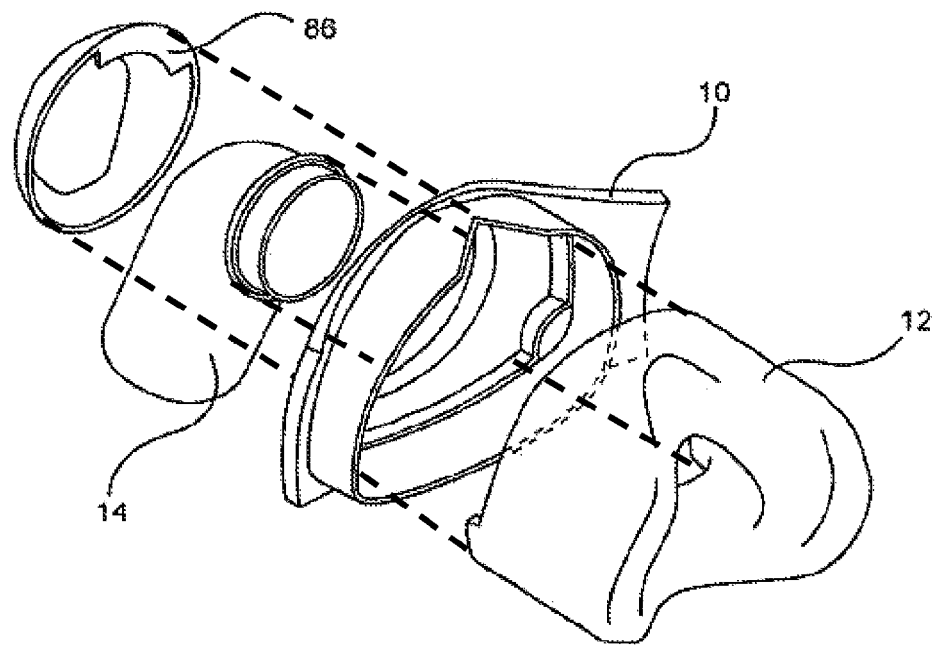
FIG. 6a-b are exploded views of one embodiment of the present invention.
Figure 6B:
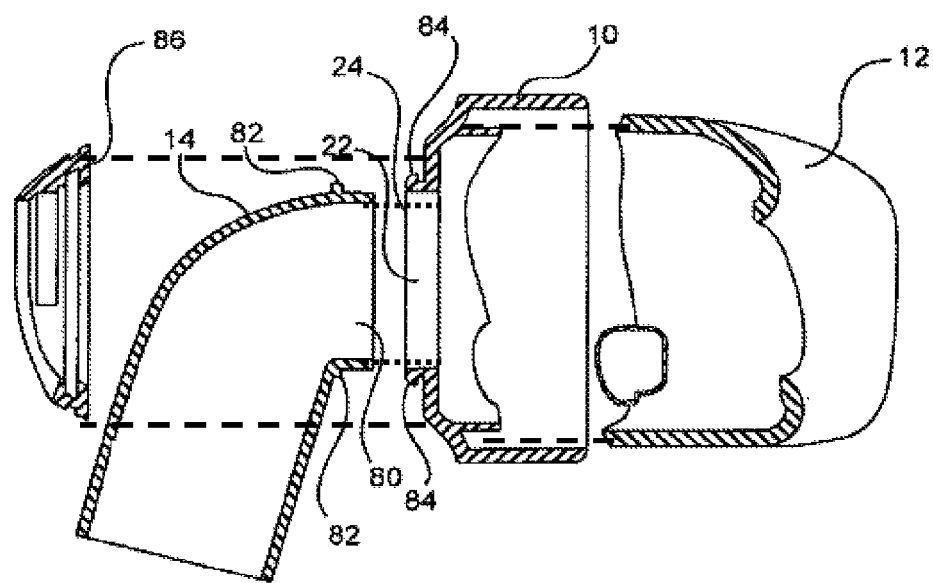

As shown in FIGS. 6*a*-*b*, in one embodiment, hose connector 14 connects to the frame 10 on a side opposite the cushion 12. The connector 14 includes a lip portion 80 which is sized to be insertable within the lip 24 and aperture 22 of the frame 10. A retaining flange 82 encircles the lip portion 80. A complementary retaining flange 84 is located on the lip of the frame 10 and it engages its counterpart on the hose connector 14 to locate the lip portion 80 within the aperture 22. A retaining ring 86 couples the hose connector 14 to the frame 10, while still allowing the hose connector 14 to rotate freely about the frame. Other known means for maintaining a rotatable connection between the hose 22 and the frame 10 may be incorporated into the present invention. The ability of the hose to rotate deflects pressure applied by the hose to the frame. This significantly reduces the ability of the hose 22 to push the mask of off the patient's face or to cause the mask to break its seal.

Figure 7:
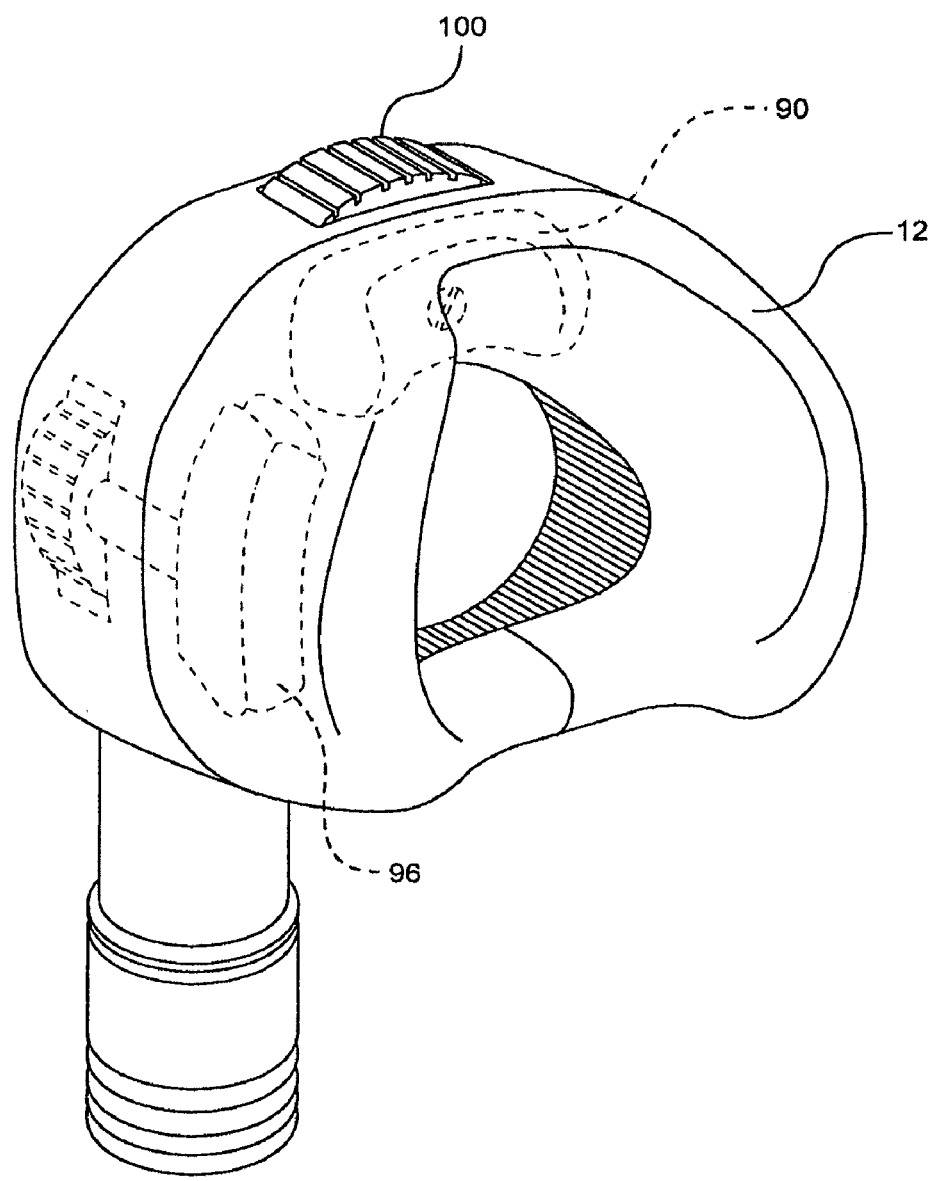
FIG. 7 is a perspective view of one embodiment of the present invention.
Figure 8:
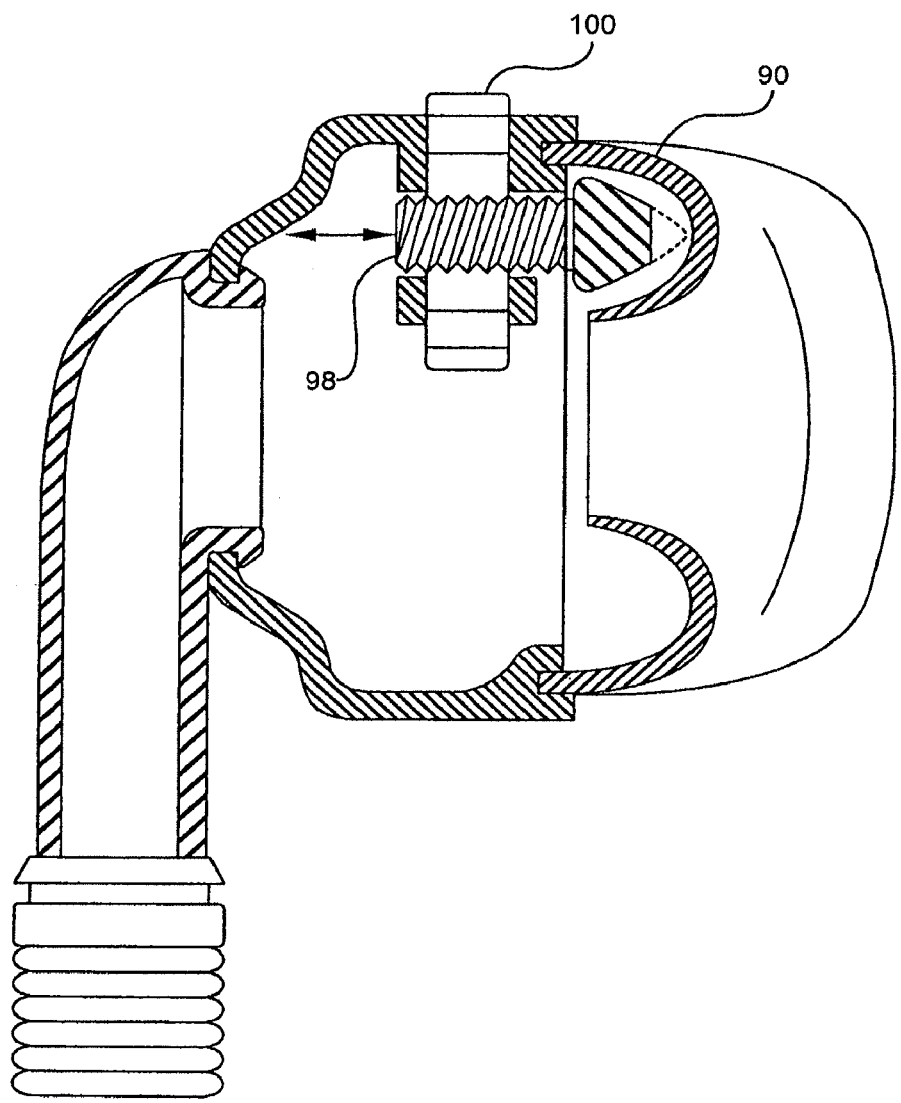
FIG. 8 is a sectional view of the embodiment of FIG. 7.
Figure 9:
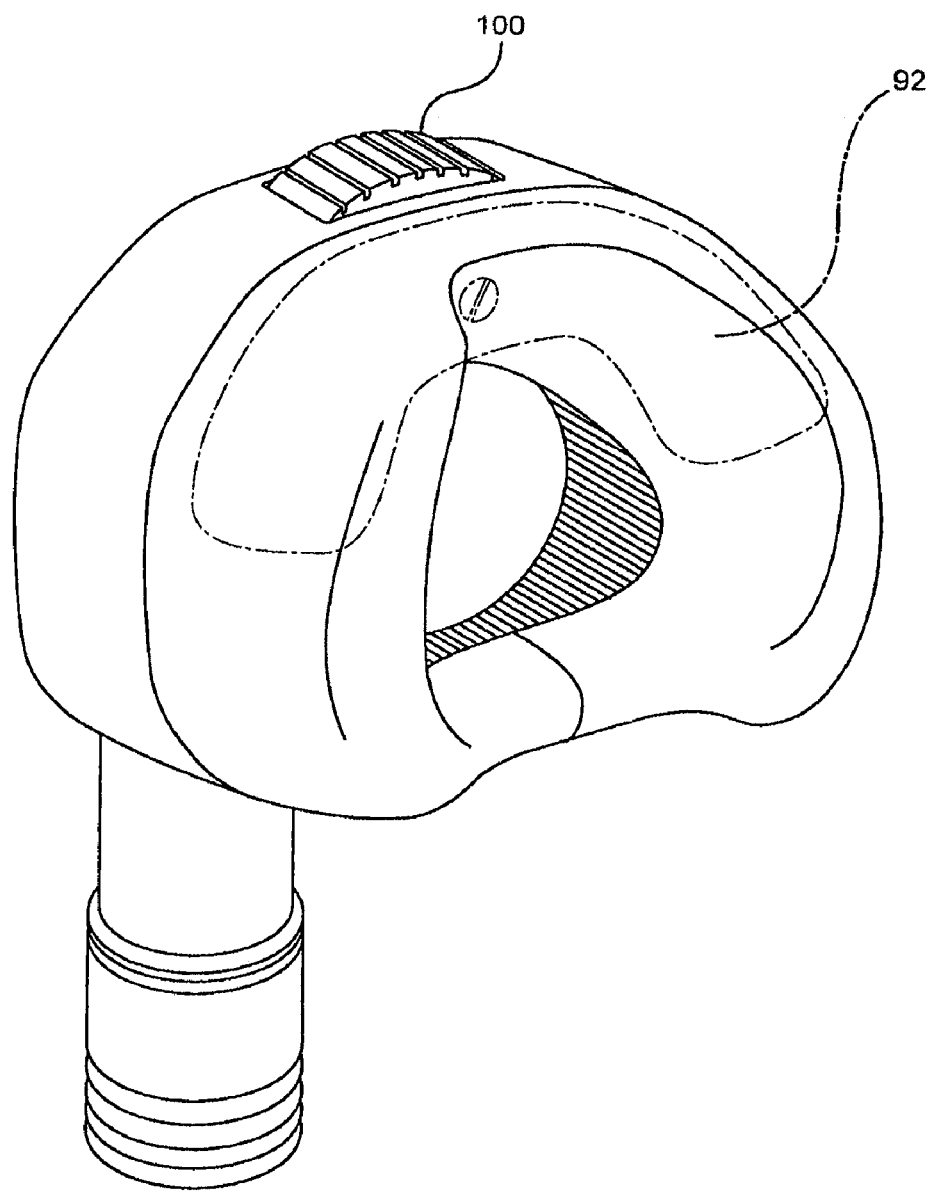
FIG. 9 is a perspective view of an alternative embodiment of the present invention.

As shown in FIGS. 7-9, in an alternative embodiment of the present invention, retractable pads 90 and 92 are used to support the cushion in the area that would contact the bridge of the nose. The pads 90 and 92 are located beneath the cushion and may be saddle shaped to accommodate the bridge of the nose. Additional pads 96 may also be included to support other areas of the cushion.

The pads 90, 92, 96 extend from or retract into the frame 10. The pad 90, 92, 96 are coupled to a stem 98, and the stem 98 is in geared communication with a wheel 100. Rotation of the wheel 100, translates the stem 98 causing it to extend from or retract into the frame 10. The pad 90, 92, 96 move in unison with the stem 98.

Figure 10:
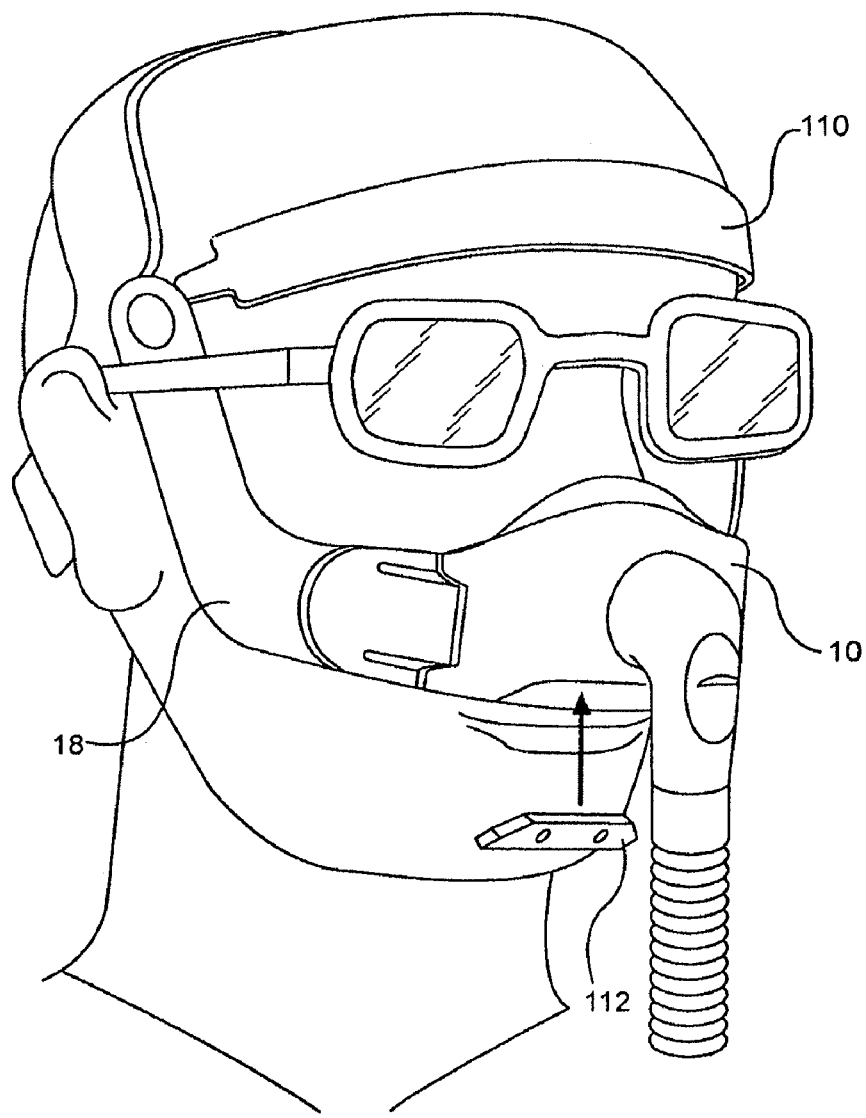
FIG. 10 is a perspective view of one embodiment of the present invention.

In another alternative embodiment shown in FIG. 10, the present invention is supplemented with physiological sensors to enable the monitoring of a patients physiological parameters during sleep. A monitoring band 110 is connected between the two base portions 61. The monitoring band 110 is positionable so that the sensors attached thereto are able to be optimally positioned. These sensors can include electroencephalogram (EEG), electromyogram (EMG), oximetry, and electrocardiogram (ECG). Furthermore, physiological sensors can be implemented in the strap 18. A thermistor 112 can also be connected to the frame 10 to detect air leaks and mouth breathing.

While the subject invention has been described with reference to several embodiments thereof, those skilled in the art will recognize various changes that may be made without departing from the spirit and scope of the claimed invention. Accordingly, this invention is not limited to what is shown in the drawings and described in the specification. Any numbering or ordering of elements in the following claims is merely for convenience and is not intended to suggest that the ordering of the elements of the claims has any particular significance.

The invention claimed is:

1. A nasal breathing mask comprising: a frame; a headgear coupled to the frame, wherein the headgear includes a pair of base portions connected by a headstrap and an arm connected to the base portion by a pivoting mechanism; a cushion coupled with the frame; wherein the cushion is an inwardly curving flexible membrane; a retractable pad being adjustably located in a direction that is generally orthogonal to the frame, wherein the pad is located beneath the cushion and adjusts to support the cushion; a stem located within the frame and removably adjustable from the pad; and a wheel in geared communication with the stem, wherein the wheel is substantially located within the frame, and wherein rotation of the wheel translates the stem inward or outward from the frame, thus moving the pad in a similar direction.

2. The mask of claim 1, wherein the pivoting mechanism includes knock out spacers on the arm and interlocking flanges on the base portion.

3. The mask of claim 1, wherein the pivoting mechanism includes a triple plate mechanism.

4. The mask of claim 1, wherein the headstrap is comprised of two separate straps connected to opposite base portions, and wherein the two straps connect to each other by a hook and loop fastener.

5. The mask of claim 1, wherein the headgear has a pair of arms and a neckstrap spanning across the arms.

6. The mask of claim 1, and further comprising a hose connector coupling a hose to the frame, the hose connector including a lip which is inserted into an aperture in the frame and a retaining ring which allows the hose connector to pivot about the frame while remaining coupled to the frame.

7. The mask of claim 1, and further comprising a strap extending from each base portion, and a connector coupling the strap to the frame, the connector including an angle adjustment mechanism which includes a first plate and a second plate coupled to each other by a pivot.

\* \* \* \* \*